(12) United States Patent
Pepper et al.

(10) Patent No.: US 6,777,244 B2
(45) Date of Patent: Aug. 17, 2004

(54) COMPACT SENSOR USING MICROCAVITY STRUCTURES

(75) Inventors: David M. Pepper, Malibu, CA (US); Daniel Sievenpiper, Los Angeles, CA (US)

(73) Assignee: HRL Laboratories, LLC, Malibu, CA (US)

( * ) Notice: Subject to any disclaimer, the term of this patent is extended or adjusted under 35 U.S.C. 154(b) by 712 days.

(21) Appl. No.: 09/732,833

(22) Filed: Dec. 6, 2000

(65) Prior Publication Data

US 2002/0068018 A1 Jun. 6, 2002

(51) Int. Cl.$^7$ ............................................ G01N 21/31
(52) U.S. Cl. .................................... 436/165; 422/82.05
(58) Field of Search ............................... 356/436, 437, 356/440; 436/164, 165, 172; 422/82.05, 82.08, 82.09

(56) References Cited

U.S. PATENT DOCUMENTS

| | | | | |
|---|---|---|---|---|
| 5,437,840 A | * | 8/1995 | King et al. | 422/82.08 |
| 5,514,596 A | * | 5/1996 | King et al. | 436/164 |
| 5,744,902 A | | 4/1998 | Vig | 310/360 |
| 5,835,231 A | | 11/1998 | Pipino | 356/440 |
| 5,866,430 A | | 2/1999 | Grow | 436/172 |
| 5,907,765 A | | 5/1999 | Lescouzeres et al. | 438/49 |
| 5,910,286 A | | 6/1999 | Lipskier | 422/68.1 |

FOREIGN PATENT DOCUMENTS

| | | |
|---|---|---|
| DE | 4230087 | 3/1994 |
| WO | 99/45357 | 9/1999 |
| WO | 01/40757 A2 | 6/2001 |
| WO | 02/01147 | 1/2002 |

OTHER PUBLICATIONS

Rosenberger, A.T., et al., "Evanescent–Wave Sensor Using Microsphere Whispering–Gallery Modes", *Laser Resonators III*, Proceedings of SPIE, vol. 3930, pp. 186–192 (2000).

Bucher, Doris J., et al., "Detection of Influenza Viruses through Selective Adsorption and Detection of the M–Protein Antigen", *Journal of Immunological Methods*, vol. 96, pp. 77–85 (1987).

Diefes, R.S., et al., "Sample/Reagent Adsorption on Alumina Versus Pyrex Substrates of Microfabricated Electrochemical Sensors", *Sensors and Actuators B 30*, pp. 133–136 (1996).

Lee, Jiunn–Fwu, et al., "Shape–selective Adsorption of Aromatic Molecules from Water by Tetramethylammonium–Smectite", *J. Chem. Soc., Faraday Trans.* 1, vol 85, No. 9, pp. 2953–2962 (1989).

Petsch, D., et al., "Membrane Absorbers for Selective Removal of Bacterial Endotoxin", *Journal of Chromatography B*, vol 693, pp. 79–91 (1997).

Pipino, Andrew C.R., "Ultrasensitive Surface Spectroscopy with a Miniature Optical Resonator", *Physical Review Letters*, vol. 83, No. 15, pp. 3093–3096 (Oct. 11, 1999).

* cited by examiner

*Primary Examiner*—Jeffrey Snay
(74) *Attorney, Agent, or Firm*—Ladas & Parry

(57) ABSTRACT

A compact sensor for detection of chemical and/or biological compounds in low concentration. The sensor comprises electromagnetic microcavities. The agent to be detected passes the microcavities, is absorbed and/or absorbed by the microcavities, and modifies the electromagnetic field inside the microcavities. After the agent has been adsorbed and/or absorbed, a probe beam is applied to the microcavities. The change of electromagnetic field is detected by the detector, and the frequency of the probe beam at which the resonance is observed, is indicative of a particular agent being present. A method for detecting chemical and/or biological compounds using the sensor.

59 Claims, 10 Drawing Sheets

COMPACT SENSOR USING MICROCAVITY STRUCTURES

BACKGROUND OF THE INVENTION

1. Field of the Invention

This invention relates to the field of compact devices for remotely detecting the presence of chemical or biological agents using an electromagnetic microcavity element or an array or assembly of microcavity elements.

More particularly, it pertains to the devices which detect chemical or biological agents using a state-selective material which is placed inside or surrounding the microcavities. The complex dielectric constant of the microcavities is modified by the presence of the compound to be detected. This invention allows one to detect the presence of chemical and biological agents even at a very low concentration.

In other terms, this invention pertains to a photonic bandgap crystal, the dispersion characteristic of which are modified by the introduction of a chemically or biologically active material, followed by the detection of such modification. The changes in the cavity in the presence of the chemical or biological species can be detected using optical, infrared, or RF probe beams, or a combination thereof.

2. Description of the Related Art

A number of techniques have been tried in prior art for detection of chemical and/or biological agents at low concentrations. For instance, single-pass absorption cell techniques have been used for species classification. Multi-pass cells are also usable for the detection of the species at low concentration.

The simplest example of a multi-pass cell is the White Cell, which consists of a pair of mirrors or diffractive elements that enable a probe beam to reflect multiple times through the same cell volume, enabling one to detect dilute quantities of a substance.

However, the standard White Cell is much larger than the microcavities of this invention, and it can be difficult to tune a large cavity to a precise resonance frequency. In addition, a White Cell typically has a lower number of passes through the sample (on the order of 10 to 100), whereas one of the attractive features of this invention is, as shown below, that a microresonator of this invention can have up to 10,000,000 passes.

Another kind of technique to make a highly selective chemical sensor is taught in U.S. Pat. No. 5,910,286 to Lipskier. Lipskier discloses a chemical sensor having an acoustic wave transducer and a layer of a molecular fingerprint material, the latter comprising a sensitive layer making the sensor highly selective. This material is a macroporous cross-linked product having cavities steric and functional configuration of which is specifically suited to capturing molecular or ionic species, or both. Lipskier teaches how to make the selective material capable of capturing the compound to be detected via an absorption or adsorption process.

Other selective surfaces have also been described. For example, use of polymers as such selective surfaces was described by D. Bucher, et. al. in "Detection of Influenza Viruses Through Selective Adsorption and Detection of the M-protein," J. Immunol. Methods, 96, p. 77 (1987). Use of ceramics was disclosed by R. Diefes, et. al. in "Sample/Reagent Adsorption on Alumina Versus Pyrex Substrates of Microfabricated Electrochemical Sensors," Sensors and Actuators, B30, p. 133 (1996). Use of complex organic compounds was taught by J-F. Lee, et. al. in "Shape-Selective Adsorption of Aromatic Molecules from Water by Tetramethylammonium Smectite," J. Chem. Soc. Faraday Trans., I85, p. 2953 (1989). Finally, use of membranes was described by D. Petsch, et. al. in "Membrane Adsorbers for Selective Removal of Bacterial Endotoxin," J. Chromatography B693, p. 79 (1997).

However, neither Lioskier nor Bucher, Diefes, Lee or Petsch discuses the electromagnetic cavity resonance effects which are extremely important in detection of even trace amounts of the compound in question.

U.S. Pat. No. 5,907,765 to Lescouzeres, et. al. discloses a method of patterning a cavity over a semiconductor device in order to manufacture a chemical sensor. This method involves forming a sacrificial layer over a substrate followed by patterning and etching this layer so that a portion of it remains on the substrate. The substrate and the remaining portion of the of the sacrificial layer are then covered by an isolation layer over which a conductive layer is formed. The conductive layer serves a purpose of providing a heater for the sensor device. The remaining portion of the of the sacrificial layer is then selectively etched away forming a cavity between the isolation layer and the substrate. This cavity provides thermal isolation between the heater and the substrate.

Lescouzeres, et. al. do teach how to form a cavity, but the purpose of the cavity is thermal isolation. Lescouzeres, et. al. do not use the cavity for enhancement of the probe electric field. Nor do they make any reference to selectivity of frequency or electromagnetic enhancements.

U.S. Pat. No. 5,866,430 to Grow discusses methods and devices for detecting, identifying and monitoring chemical or microbial species using the techniques of Raman scattering. Grow's methodology includes four steps: (a) the gas or liquid to be analyzed or monitored is brought into a contact with a bioconcentrator, the latter being used for binding with the species or for collection or concentration of the species; (b) the bioconcentrator-species complex is irradiated at one or more predetermined wavelengths to produce the Raman scattering spectral bands; (c) the Raman spectral bands are processed to obtain an electric signal; and (d) the electric signal is processed to detect and identify the species, quantitatively, qualitatively, or both.

The Grow invention uses a Raman Optrode instrument comprising a Raman spectrometer capable of collecting and processing the Raman scattering spectral information and converting it into electrical signals. This method uses Raman Spectroscopy for the analysis. It teaches the use of a bioconcentrator which utilizes adsorption and absorption techniques. However, Grow does not disclose any use of the field enhancement cavities.

U.S. Pat. No. 5,835,231 to Pipino discloses a broadband, ultra-highly sensitive chemical sensor which detects chemicals through the use of a small, extremely low-loss, monolithic optical cavity fabricated from highly transparent, polygonally shaped optical material. Optical radiation in this invention enters and exits the monolithic cavity by photon tunneling in which two totally reflecting surfaces are brought in a close proximity. In the presence of an absorbing material, the loss per pass is increased and the decay rate of an injected pulse is determined. The change in decay rate is used to obtain a quantitative sensor with sensitivity of 1 part per million per pass or better. A similar idea was also described by A. Pipino in "Ultrasensitive Surface Spectroscopy with a Miniature Optical Resonator," Phys. Rev. Let., Vol. 83, No. 15, p. 3093 (1999).

Pipino does use the concept of optical field enhancement in a cavity; however, he uses only a single microcavity and an array. Thus, Pipino does not allow the enhancement effect to occur over a broad area, nor does he teach any means of attracting or concentrating the species to be detected.

Finally, U.S. Pat. No. 5,744,902 to Vig discloses a chemical or biological sensor formed from a coated array. Both mass and temperature changes due to the presence of a particular substance or agent causes a change in output frequency, which change is linked to the analyzed species. Furthermore, the change in frequency output due to the mass loading is distinguished from the change due to the temperature change. Vig teaches arrays of microresonators; however, his resonators are mechanical and not electromagnetic ones.

However, the subsequently discussed microresonators of this invention, have serious advantages compared to those of the Vig's invention. Probing the microcavities optically is easier, the sensitivity may be greater, and this invention offers a means to probe remotely, using an optical or RF-beam. Vig does not have such remote probing feature.

There is a need to have compact, low cost remote sensors of chemical and/or biological species which:

(a) are very sensitive in proportion to their compact size and are able to detect very small quantifies of the compound in question;

(b) can be scaled to function in the visible portion of the spectrum, throughout the infra-red portion and into the teraherz or microwave region;

(c) can be easily fabricated using standard photolithographic techniques on a variety of substrates;

(d) can be fabricated as a monolithic planar devices integrated into a waveguide structure, or configured as volumetric sensors;

(e) are lightweight;

(f) can be employed on a unmanned air vehicle (UAV) or $\mu$-UAV platforms for remote sensing;

(g) can detect multiple resonances within a substance, or multiple substances;

(h) can be made to ignore false positive results (anti-spoofing);

(i) can be made to have self-calibrating capabilities;

(j) can have a larger lifetime and a higher production yield; and (k) are expendable.

Compact sensors using microcavity structures satisfy all these requirements. Previously, known sensors required long interaction lengths to enable detection of small amounts of a given species. Therefore, there was a need for cumbrous white-cell configurations where the substance to be detected is to pass the structure multiple times.

The concept of the state-selective microcavity array leads to production of a novel biochemical sensor. As will be shown below, the present invention avoids problems associated with previously known sensors by using electromagnetic cavity resonance effects and by enhancing the electromagnetic field of the species being analyzed.

There exists no known prior art for compact sensors using microcavities for enhancement of the probe electromagnetic field. Yet the need for such is acute.

For the foregoing reasons, there is a necessity for a compact low-cost sensor for detection of very low amounts of chemical and/or biological substances using microcavities. The present invention discloses such sensors.

SUMMARY OF THE INVENTION

The present invention is directed to a compact sensor of chemical and/or biological agents using microcavities. The agent to be detected passes the microcavities and modifies the properties of the microcavities, or, in another embodiment, is capable of being detected because the sensitivity of the device is greatly enhanced by the microcavity.

When attempting to detect a biological or chemical species, one crucial factor is the sensitivity of the detector to dilute concentrations, because some of most dangerous biological toxins can be lethal at levels of only a few parts per billion, and bacteria or viruses can achieve infection with a very small number of organisms. These minuscule doses needed to achieve a lethal outcome lead to a challenging problem in detection, as the human detector may reveal symptoms at concentrations far below what an electronic detector or other classes of sensors can register.

In optical, infrared, or millimeter wave sensing, detection often means sensing a change in the amplitude or phase of a wave which is passing through or reflecting off of the material under test. Examples include passing a probe beam through the air, or reflecting the wave off of the ground or other surfaces, and looking for particular absorption lines.

If the substance to be detected is very dilute, its effects may fall below the noise floor of the detection system. One can address this problem by sampling the material many times with a single probe beam, such as in an optical cavity. Any absorption or phase shift of the probe beam will be effectively multiplied by the Q factor of the cavity, resulting in a stronger signal.

To achieve cavity enhancement of a visible, infra-red, or millimeter wave signal does not necessitate having large cavity structures with precisely aligned mirrors. The same effects can be seen in many naturally occurring forms. For example, in surface-enhanced Raman spectroscopy, as little as a few molecules can be detected simply by adsorbing them to a metal surface. The natural roughness of the metal surface creates micron-scale hills and valleys which can be seen as tiny optical cavities.

When a molecule falls into one of these natural microcavities, the electric field of the probe beam is enhanced by the walls of the cavity resulting in a much stronger received signal. This is equivalent to sampling the same molecule many times with a single probe beam. Although Raman spectroscopy relies on non-linear optical effects the same enhancement also applies to linear effects such as optical absorption.

While a rough metal surface clearly provides some absorption enhancement to chemicals on the surface, it does so in a random, uncontrolled manner. If one wishes to sense a variety of biological or chemical species, each with a distinct electromagnetic signature, a broadband source is required. With a random assortment of natural microcavities, the received signal would be an unintelligible spectrum containing a superposition of the electromagnetic signatures of all nearby compounds or organisms.

A more sensible approach involves applying this knowledge of microcavity electromagnetic enhancement with modern fabrication techniques to create a detector with well-defined properties. Such a detector would consist of an array of microcavities which would be designed to sense only a single absorption line of a particular species or chemical, or a set of well-defined spectral features which, collectively, act as a unique "fingerprint" of the species to be detected.

This would be achieved by selecting the resonance frequency of the microcavities to coincide with a resonance of the material to be detected. The selectivity of the detector is enhanced if it is coated with a gel which selectively adsorbs certain chemicals or organisms, while rejecting others. By combining many such arrays with different resonance frequencies into a single detector, it could detect a variety of different species. Integrated with electronic logic circuits, this detector would be insensitive to "false positive" readings from other substances. The entire sensor array could be produced using photolithographic and MEMS processing techniques, and assembled into a chip-scale package, with many of the components residing on a single monolithic substrate.

A microstructure possesses a Q characteristic which can be defined in a number of ways. Q is a ratio between energy stored inside cavities and energy lost per cycle. For the purposes of this invention Q can also be interpreted as $$Q = E_c^2 / E_b^2,$$

where $E_c$ is the electromagnetic field inside the cavities and $E_b$ is electromagnetic field of the probe beam.

Q can also be looked at as a number of equivalent passes of the probe beam inside the cavity, for instance, the number of times the sample is probed.

The effective cavity Q of the microstructure element is large. Given this fact, the sensitivity of the structure is enhanced compared to conventional approaches.

The smallest size of the microcavities is on the order of one cubic half-wavelength. Generally, the degree of porousness for the microcavities of this invention is about one microcavity per square wavelength on a two-dimensional structure or one microcavity per cubic wavelength on a tri-dimensional structure. The size of the pores is generally smaller than a cubic half-wavelength and is related to the Q of the microcavities. If r is a radius of the microcavities and $\lambda$ is a wavelength, then $Q \sim (\lambda/r)^3$.

In one aspect, the present invention provides a process of building electromagnetic structures having microcavities. These structures have well-defined operating frequencies which are adjustable by varying the physical parameters of the cavities according to a known set of design parameters. Combining these microcavities with the state-selective absorbents, a sensor is fabricated, which first attracts and concentrates the bio-chemical substance to be measured, and then detects it with a high decree of sensitivity through the cavity enhancement effect.

The entire system is amenable to chip-scale integration with microelectronic circuits to create an intelligent sensor in a small package.

Microcavities are preferably manufactured in a form of an array. Such an array is useful because it provides a large area of microcavities. In principle, a single microcavity, especially a treated microsphere subsequently discussed, can also be used. However, an array of microcavities is preferable, because a single cavity could be more difficult to probe because of its small size.

A microcavity array may be fabricated on a surface of a passive planar structure which also contains a state-selective adsorbing material. The state-selective adsorbing material is any material which changes in response to the presence of the material to be detected. For instance, a state-selective material can be an antibody of a particular antigen which one is trying to detect.

A chemical or biological species is adsorbed or absorbed by the treated material in the structure. As a result, a transmission and/or reflectivity of the structure, determined by a probe beam, is modified in phase and/or amplitude due to the presence of a given chemical or biological species.

The basic structure comprises an array of microresonators. This structure can also be classified as a photonic bandgap crystal with a state-selective absorbing material. The structure may be in the form of a two-dimensional planar array of these elements or may be a three-dimensional volumetric ensemble of such microcavities. The device can be fabricated as a monolithic structure or individual microspheres or disks can be self-assembled onto a common substrate or attached to the end of an optical fiber bundle or RF waveguide. Yet another device architecture is a pair of waveguide channels, between which is situated a microsphere or a micro-ring resonator.

The microcavity array can also be in a form of an ensemble of micro-resonators, micro-disks, or microspheres which can be fabricated onto a common substrate using self-assembly techniques. Other three-dimensional structures can be likewise used.

Such self-assembly techniques are well known to those skilled in the art. They comprise, for example, the technique for assembly of mono-layers of dielectric spheres, in which a substrate is drawn out of a liquid, usually water, containing the spheres. The spheres then form a mono-layer on the substrate.

The system can be used for spectral analysis in the visible range, in the infra-red range or in the teraherz range, depending on the scale size of the microcavity elements. Multiple-sized elements can be easily integrated onto the same substrate for hyper-spectral analysis of more complex compounds. In such case, a more detailed spectroscopic evaluation may be needed to distinguish between similar species, which is very important since certain classes of toxic species have spectral and structural properties similar to those of their non-toxic analogs.

The array can be probed using various differential detection methods for common-mode rejection of source and environmental noise, resulting in a more robust sensor package. Various techniques can be used for improved performance, including, but not limited to, differential absorption, modulation spectroscopy, or frequency-shifted sources. These methods and techniques are well known to those skilled in the art of spectroscopy.

This patent discloses two related systems for detection of species, both of which systems are described below in detail. According to the first system, the species modifies the microcavity Q, and such modification is detected by absorption of a resonant or near-resonant probe beam. According to the second system, the microcavity is not modified, but the species affects the phase shift which is detected by sampling of the structure by a resonant or non-resonant probe, the sensitivity of which is enhanced by the high Q of the structure.

For the purposes of this disclosure, the term "resonance" is defined as a condition where the wavelength of the probe beam matches the absorption lines of the state-selective material.

Each of the two systems mentioned above can be implemented by more than one embodiment.

One aspect of this invention provides a sensor for detecting chemical and/or biological compounds comprising a first element comprising a plurality of microcavities disposed on a substrate, and a second element comprising a source of electromagnetic radiation and a detector of electromagnetic radiation, wherein the chemical and/or biological compounds are adsorbed or/and absorbed by the microcavities causing a change of electromagnetic field of the microcavities, and the change being detected by the second element.

Another aspect of this invention provides a method for detecting chemical and/or biological compounds, comprising steps of providing a substrate with a plurality of microcavities disposed thereupon, providing a probing device comprising a source of electromagnetic radiation and a detector of electromagnetic radiation, directing the chemical and/or biological compounds at the microcavities, adsorbing or/and absorbing the chemical and/or biological compounds by the microcavities causing a change of electromagnetic field of the microcavities, and detecting the change of electromagnetic field by the probing device.

BRIEF DESCRIPTION OF THE DRAWINGS

The features and advantages of the present invention will become better understood with regard to the following description, appended claims, and accompanying drawings where:

DETAILED DESCRIPTION OF THE INVENTION

1. Sensor in General

Figure 1:
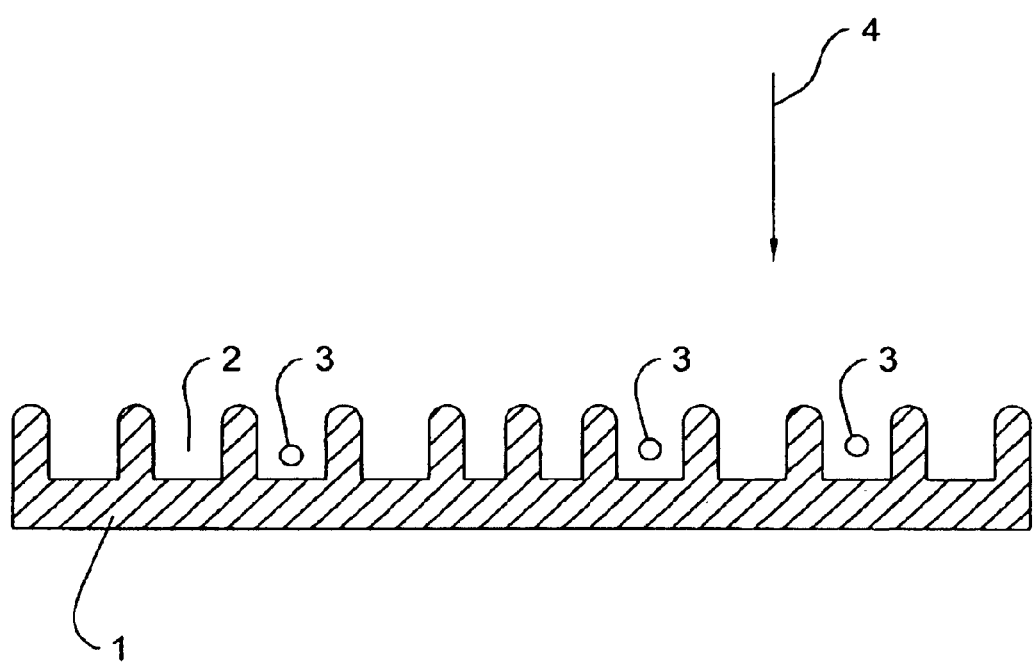
FIG. 1 is a schematic diagram showing the principle of electric field enhancement by an array of microcavities.

A simple example of an array of microcavities is shown in FIG. 1. A metal or dielectric surface 1 is textured with a lattice to form microcavities 2, into which particles of material to be detected 3 can fall. Due to the field enhancement inside the cavity 2, the absorption of the probe beam 4 is much greater than it would be if the particle were simply in a free space or on a smooth surface, as explained in more detail below.

The basic principle upon which this invention is based, is the principle of enhancement of electromagnetic field by an array of microcavities and it can be explained as follows. When a chemical compound enters one of the microcavities, it feels a much greater applied electromagnetic field when the probe beam is near the resonance frequency of the cavities. In effect, the probe beam samples the chemical compound multiple times. The magnitude of this enhancement is proportional to the Q of the cavities. This is similar to the enhancement effect seen in surface-enhanced Raman spectroscopy.

However, in this case, since the cavity 2 has a sharp resonance, the effect only occurs when the cavity 2 resonance coincides with an absorption line of the tested material 3.

Many of these basic structures involving "passive" microcavities (that is, without treating the microcavities with any state-selective absorbing material) have been investigated by others in the radio-frequency and optical regimes.

Typical applications involve optical or radio frequency filtering, reconfigurable antennas, optical multiplexing and add/drop networks, and nonlinear phase shifters for self-action effects (e.g., optically controlled add/drop channels). Many of these applications exploit the fact that these structures are capable of attaining a high-Q, so that low optical or RF powers are needed to realize the self-action effects. The local high-field enhancements in the microcavities are also somewhat similar to those previously observed in surface enhanced nonlinear optical effects, including Raman scattering and second harmonic generation.

However, in the present invention, the high-field regions are fabricated into the basic structure in a deterministic manner via photolithographic techniques, so that each structure can be easily and reliably reproduced, and their properties well defined.

In its most general form, the sensor of this invention comprises an array of electromagnetic microcavities 2 that include a material that specifically attracts the agent to be detected 3. The microcavities 2 can be designed to resonate at the same frequency, or at different frequencies.

If the cavities 2 are designed to resonate at the same frequency, which is a preferable design, the frequency to be used is a frequency where the agent to be detected 3 absorbs electromagnetic radiation. The single-resonance version design is simpler than the different-resonance version and is, therefore, more cost effective. As an alternative, the cavities could be designed to resonate at a frequency where the chemical combination of the agent to be detected 3 and the attracting material absorbs electromagnetic radiation when the two substances come in contact.

If the microcavities 2 are designed to resonate at different frequencies, then these frequencies should be chosen to coincide with various absorption bands of the agent to be detected 3 (or absorption bands of the chemical combination of the agent to be detected 3 and the attracting material). The version with microcavities having different resonance frequencies may give more accurate results than the same-resonance version.

Furthermore, the resonance frequencies of the microcavities 2 can be designed to include frequencies that do not fall within absorption bands of the agent to be detected 3, so that the absence of absorption within these bands can serve to prevent false positive results.

Another benefit of a sensor with differing cavity resonances (that do and do not overlap the specific agent to be sensed) is that there may be scenarios where broadband background absorptions may exist, such as propagation-path scattering, as well as gradual degradation of the sensor apparatus (e.g., source fluctuations, detector drifts, etc.). In this case, one can provide for common-path referencing via post-processing (e.g., phase and/or amplitude differencing) of the signals from the on-resonant and off-resonant cavity elements.

Figure 2:
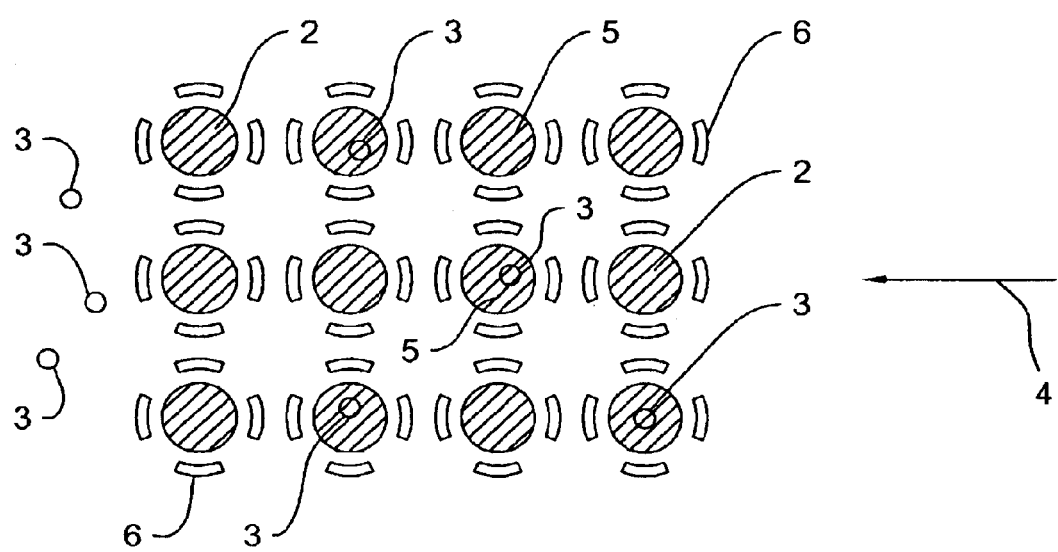
FIG. 2 is a schematic diagram illustrating the mechanism of enhancement of the electromagnetic field inside the microcavities.
Figure 3:
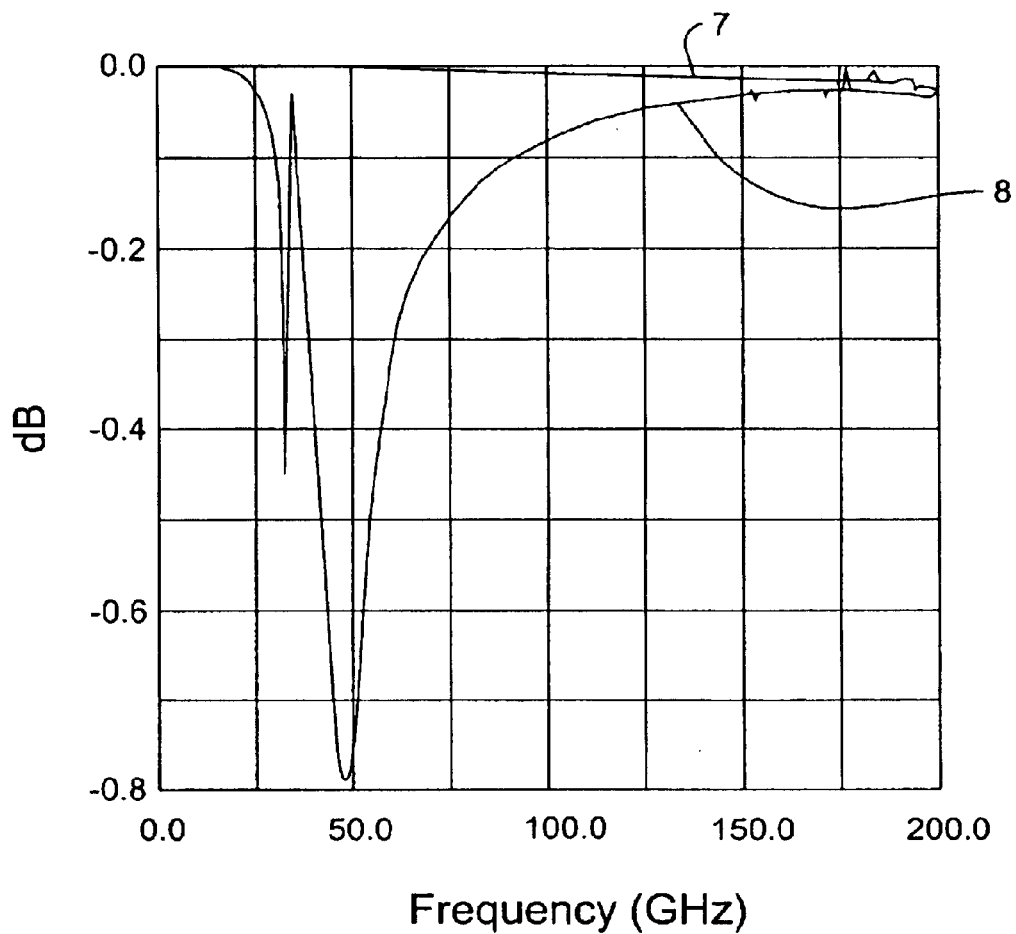
FIG. 3 is a chart showing the cavity enhancement effect.

In either case, whether the sensor is designed with cavities resonating at the same frequencies, or with cavities resonating at different frequencies, the mechanism of enhancement of the electromagnetic field inside the cavities is the same and is illustrated in FIG. 2.

The microcavities 2 of the sensor are treated with a material 5 that can selectively adsorb a desired chemical or biological compound 3 to be detected. The impedance of the structure will be changed when the desired compound 3 becomes bonded or linked to the cavities 2. Given the high Q of the device, the sensitivity of the sensor is significantly enhanced by a factor approaching the Q of the microcavity. In essence, the microcavity enables a probe beam 4 to pass the species multiple times, increasing the device sensitivity. Microcavity's Qs are within the range of between about thousands to more than about ten million, so the enhancement can be significant.

Such a sensor can be used over large-regions of the radio-frequency/optical spectrum, depending on the scale size of the microcavity, the desired probe wavelength, and the specific state-selective material. Sources can include narrowband lasers as well as teraherz radiators.

The mode of operation of the sensor of this invention having either type of the cavity discussed above can be described as follows.

If all the microcavities 2 are designed to resonate at the same frequency, then they simply serve to enhance the signal obtained from this detector, in comparison to conventional electromagnetic detectors. This enhancement occurs for two reasons:

(1) the electromagnetic field is enhanced within specific regions within the microcavities 2; and
(2) concentration of the agent to be detected 3 within this same region of the cavities, due to the presence of an attracting material 5.

This mechanism of enhancement can be understood by the following description. First, the electromagnetic cavities cause an increase in the electric field of the probe signal at certain locations within the cavity. The probe beam 4 spends more time inside the cavity than it would if it were passing through the same distance of free space, as it is reflected many times by the walls of the cavity before escaping. The enhancement factor is roughly equal to the Q of the cavity, which depends on its specific design, and can range from tens to millions or more.

If the agent to be detected 3 falls within this region of such a cavity, then any electromagnetic absorption by the agent 3 is enhanced by the same amount that the electric field is enhanced. This statement assumes that the absorption occurs through an electric dipole mode of the agent or of some chemical species within the agent. This absorption enhancement can only occur if the agent 3 falls within the cavity, so it is necessary to concentrate the agent 3 into the same regions as where the electric field enhancement occurs.

Thus, the second way in which the signal is enhanced is by placing a material within the cavity that attracts the agent to be detected. This material is chosen specifically to be selective toward the agent to be detected, or to a class of agents which are of interest. The total signal enhancement is then equal to the Q of the cavities, multiplied by an absorption efficiency factor that describes the increase in the agent concentration within the cavities compared to the surrounding space.

As shown on FIG. 2, the microcavities 2 are arranged in a 3-D lattice. In this case, the material works in transmission mode. A probe beam 4 propagates through the material, and the electromagnetic field 6 is enhanced in the microcavities 2, which are impregnated with a state-selective material 5 that absorbs the compound to be detected 3. The state-selective treatment of the microcavities can be realized by treating their surface or by treating their volume, the latter in the case of a solid microcavity (e.g., a solid microsphere).

A computer simulation of the cavity enhancement effect, performed using HP-HFSS software, is shown in FIG. 3. The simulation comprised a structure of a single unit cell of an array of metal microcavities patterned on a metal surface. A small amount of adsorbing material 3, modeled as a lossy dielectric, was placed within the cavities 2. The curve 8 shows the reflection magnitude of the surface, which exhibits measurable loss at the resonance frequency of 50 GHz. If the same volume of lossy material is measured without the cavity, the curve 7 is produced. In both simulations, the lossy material is broadband, and does not have a distinct absorption line. In practice, the resonance frequency of the microcavity array would be tuned to match the absorption lines of the material to be detected.

At the cavity resonance frequency of about 50 GHz, the absorption is increased to the point where it would be measurable. Without the cavity 2, the lossy material 3 is nearly undetectable. This simulation is performed at millimeter wave frequencies, but the same results would be applicable to teraherz, infrared or optical frequencies, scaling with the dimensions of the cavity 2.

2. Operation, Basic Implementations and Various Possible Embodiments of the Sensor The operation of the sensor is described as follows. The sensor comprises microcavities 2 containing a material 5 that attracts the agent to be detected 3. The sensor is then placed in an arrangement with a source of electromagnetic radiation (not shown), from which the probe beam 4 emanates, and a detector of electromagnetic radiation (not shown).

The source of electromagnetic radiation is a laser or a RF-oscillator, operating in the visible, teraherz, infrared, or ultraviolet spectral regions, depending on the specific agent to be detected or a light emitting diode if the structure is designed to work at optical frequencies. It could also be any other optical light source, such as an incandescent, fluorescent, or phosphorescent source.

The detector is a photodiode, or any other photodetector, operating in any of microwave, teraherz, infrared, visible light and ultra-violet ranges of frequencies. Each of these sources and detectors are known to those skilled in the art of optics.

If the structure is designed to operate at microwave frequencies, then the source is a microwave source, and the detector is a microwave detector. Both devices are known to those skilled in the art of radio-frequency or microwave circuits.

It could also operate in the teraherz range, which falls between optical and microwave frequencies. Sources and detectors also exist in this range, which are known to those skilled in the art of teraherz radiation. This invention is not limited to a particular type of electromagnetic radiation, or to a particular source or detector. Locations of the source and detector of radiation depend on particular application of the sensor and are known to those skilled in the art.

The microcavity structure can also be a "multiply resonant structure," if the species to be detected has a multi-step molecular energy excitation mechanism or a non-linear spectrally enhanced feature to be probed.

After the microcavity structure with the attracting material 5 is arranged with the radiation source and detector, the unit is exposed to the agent to be detected 3. This is done preferably by pumping air through the unit which is suspected to contain the agent of interest 3, or by pumping water or other liquid over the microcavity structure which is suspected to contain the agent of interest. Alternatively, the agent 3 can also be passed from air to liquid by rapid aeration of the liquid. There is a variety of existing liquid and vapor transport devices available for this function, including conventional pumps, as well as miniature microelectromechanical (MEMS) devices. These liquid and vapor transport devices as well as the MEMS devices are known to those skilled in the art.

After exposing the microcavities 2, they are preferably illuminated by the radiation source which source generates the probe beam 4. The radiation passes through the microcavities 2, or reflects off the microcavities 2, as the case may be, and is received by the radiation detector. A reduction in received signal is taken as a positive result, and the microcavities 2 are assumed to contain the agent of interest 3 which has absorbed the radiation.

Alternatively, two such tests can be conducted in parallel, such that one set of microcavities is exposed and a second set of microcavities is not. In this case, both sets of microcavities 2 are illuminated, and the differential signal is used to determine if the agent of interest is present. This method can be used to cancel the effects of variations in the performance of the radiation source or detector. Depending on the properties of a particular state-selective material, it may need to be re-applied after each use or it may be reusable.

Another embodiment of the sensor invention is a version in which each of the microcavities 2 have different resonance frequencies, or the microcavities 2 are clustered into groups, with each group having a different resonance frequency. This method provides for a more accurate detection system, because if the agent 3 to be detected absorbs in multiple bands, then each of these absorption bands could be probed.

Furthermore, if the agent 3 does not absorb in specific bands, then these bands could be used to prevent false positive results. This would consist of multiple parallel copies of the structure described above, with each tuned to a specific frequency band. They could be fabricated on the same substrate 1, or fabricated separately and then assembled. The preferred material for substrate 1 is glass having a thickness preferably of at least about 1 millimeter.

Each microcavity would be preferably illuminated in parallel, and each would be associated with a specific detector. As an alternative for this embodiment where microcavities 2 have different resonance frequencies, the array of microcavities could be scanned sequentially by a single source or detector. If a reduction in received electromagnetic energy is obtained from a certain subset of microcavities 2, and this subset corresponds to only those frequencies where the agent to be detected 3 is known to absorb electromagnetic radiation, then a positive result is obtained.

However, if certain frequencies do not show a reduction in received energy, but the agent to be detected 3 is known to absorb at those frequencies, then a negative result is obtained. Furthermore, if certain frequencies show a reduction in received energy, but the agent to be detected 3 is known to not absorb at those frequencies, then another agent may also be present.

Yet another embodiment of this invention is one in which the microcavities 2 contain a material that attracts multiple agents 3. Then the procedure above is performed on all of the microcavities 2, and the results are cataloged by frequency. If the microcavities 2 that showed absorption correspond to the absorption frequencies of a particular agent 3 of interest, then a positive result is obtained for that agent 3. This can be important if multiple agents 3 may be present at the same time.

There are two basic device implementations (with several embodiments for each implementation), a near-resonant approach and an off-resonant scheme. In this context, "resonance" is defined as a condition where the wavelength of the probe beam 4 matches the absorption lines of the state-selective material 5.

Under the resonant or near-resonant implementation, the species to be sensed 3 will modify microcavities, which modification can be probed via absorption or reflection of the structure by a near-resonant probe beam 4.

In the off-resonant embodiment, the agent 3 does not modify the microcavities 2, but, instead, affects the phase shift experienced via sampling of the structure with an off-resonant probe, whose sensitivity is enhanced by the high Q of the structure. In this latter case, one can view the sensor as a very compact and rugged solid-state White Cell, without the need for bulk microcavities or alignment. In one embodiment of the off-resonant approach, a doped microsphere or micro-ring resonator can be used to couple a probe beam between a pair of optical waveguides (two fibers, or two channel planar waveguides). When the system is exposed to the desired species, the phase shift would be modified, and the coupling strength affected. This scheme can be biased so that, in the absence of the species, one detects a zero level, which can reduce the noise background.

In another embodiment of the off-resonant approach, assuming that the resonant feature is in the teraherz region and that a semiconductor-based structure (e.g., Si, GaAs, etc.) is employed, the device would thus be transparent to the teraherz radiation, expect in the region of the doped microcavity array. This would enable one to probe the structure from a variety of directions, and, potentially, to employ diffractive elements to realize a compact geometry.

Figure 4:
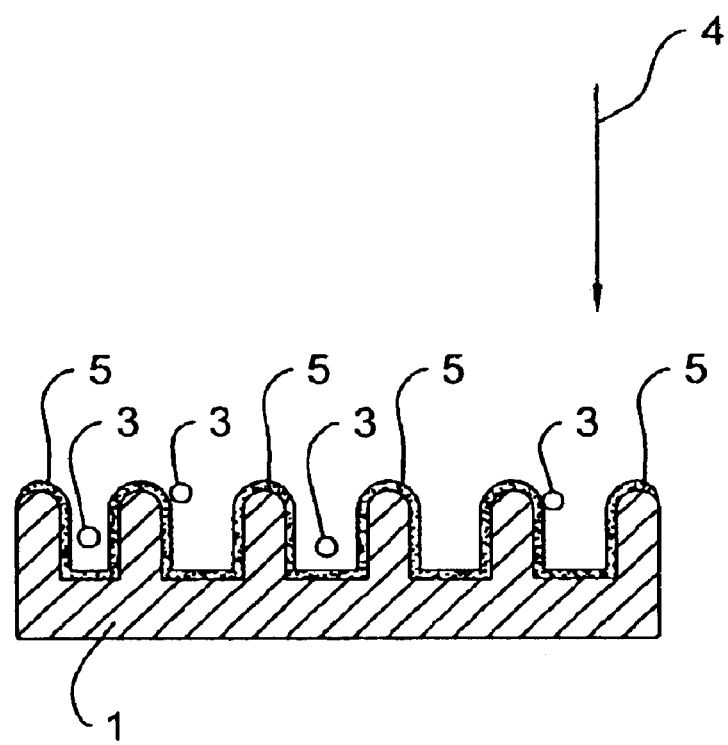
FIG. 4 is a schematic diagram showing microcavities in conjunction with surface texture created using the "LIGA" technique.
Figure 5A:
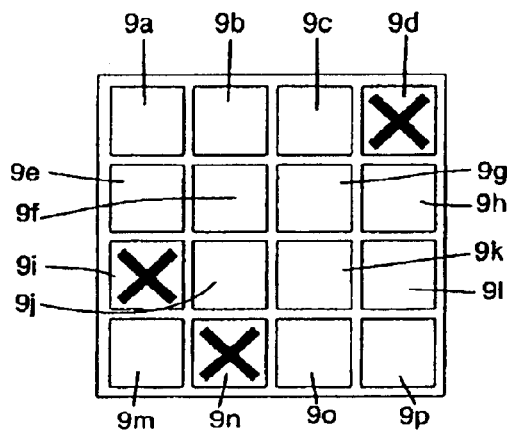
FIGS. 5(a) and 5(b) are diagrams schematically showing a method of distinguishing different chemical and/or biological species by their absorption spectra.
Figure 5B:
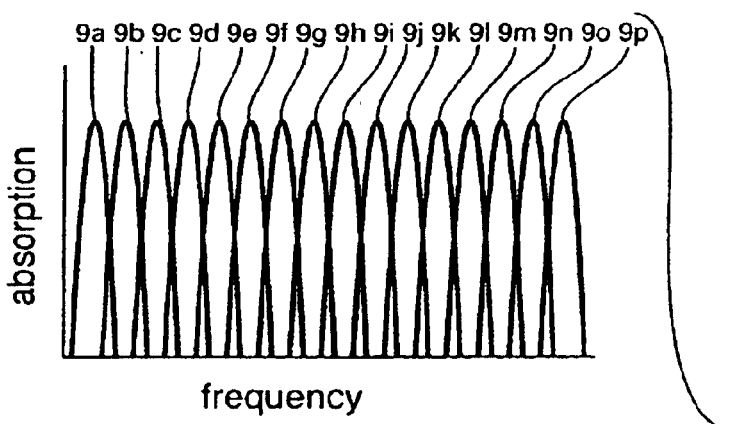
Figure 5B:
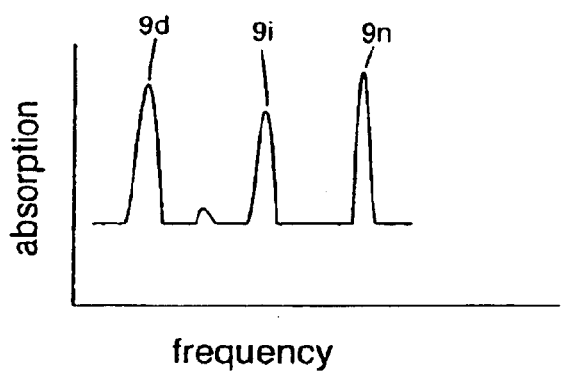
Figure 6:
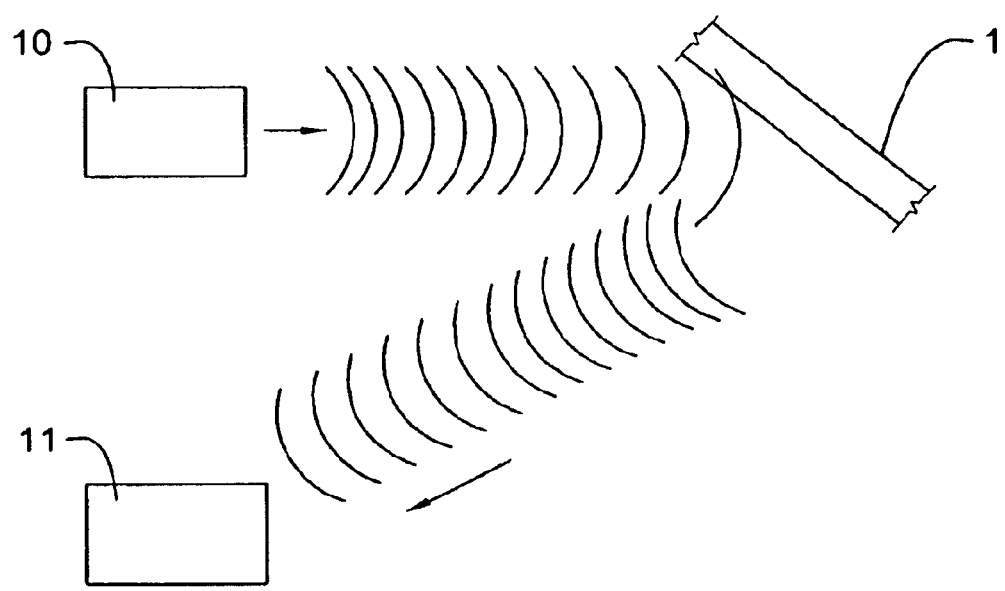
FIG. 6 is a schematic diagram showing a method of detection of various chemical and/or biological species using a broadband source and a broadband detector.
Figure 7:
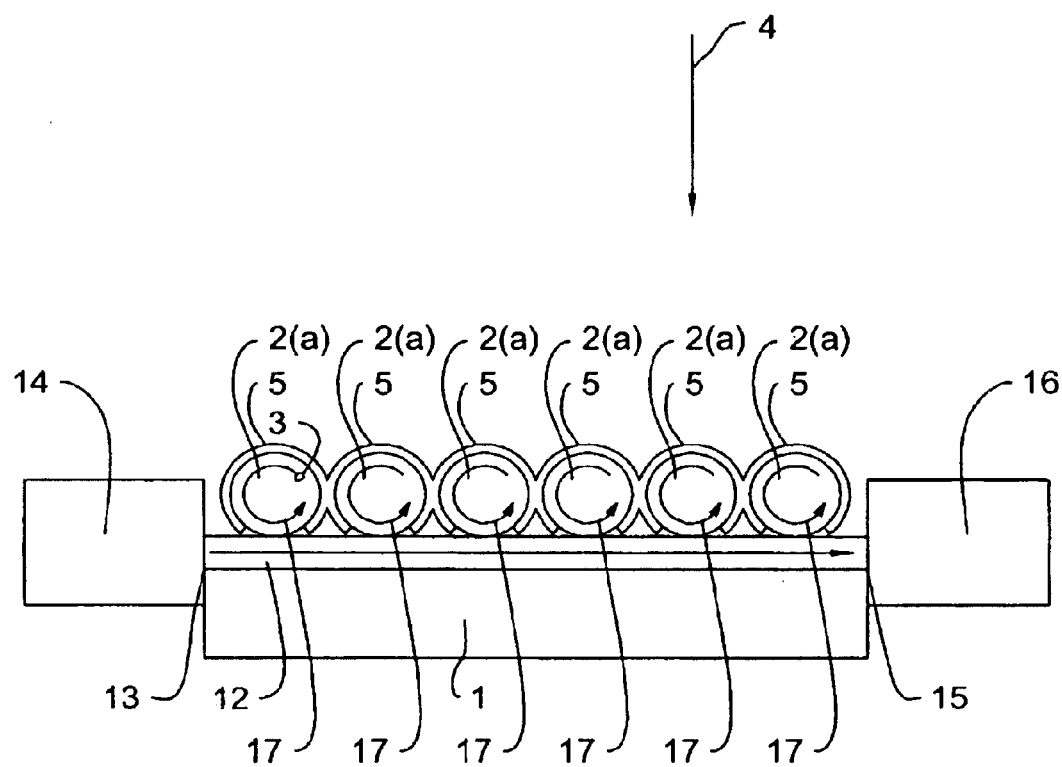
FIG. 7 is a schematic diagram showing a preferred embodiment of the sensor, with an array of microcavities arranged on a substrate with a planar optical waveguide.

Yet another embodiment of the off-resonant approach is a planar (two-dimensional) photonic-crystal reflective structure, shown in FIG. 4, the radiation pattern, polarization, and/or reflectivity of which can be modified by the adsorption of the foreign species. This structure includes a more sophisticated surface texture which can be created using techniques such as "LIGA." The "LIGA" technique, well known to those skilled in the art of micromachining, combines electroplating of metals with patterning and etching of sacrificial dielectrics to produce sub-micron scale metal structures. By fabricating a teraherz or optical scale high impedance surface ("Hi-Z surface"), one can create a structure with a resonance frequency and bandwidth which are determined by geometry. Such structures are characterized by a known set of design parameters. By coating the surface with a state selective gel which adsorbs chemical or biological species, one can concentrate the material to be detected in the region of enhanced electric field.

Again, using a dual probe scheme, an in situ calibration can be realized, so that global perturbations can be corrected in real-time. One can thus perform ellipsometry on this structure to infer the presence of the foreign species.

As a variation of this reflective embodiment, a waveguide structure can be assembled using the planar reflective component the waveguide structure comprising a waveguide wall, a coupler, or an end-cap. In this case, a radio-frequency probe signal that is coupled into the structure will be affected by the presence of the desired compound, since the waveguide dispersion will be modified by the adsorption of the chemical or biological material by this molecular-controllable radio-frequency structure.

In the general system, the sensor is probed using a differential signal/reference approach. In this case, the signal beam would be modified by the structure (e.g., a structure experiencing a phase shift, polarization rotation, or absorption change), while the probe beam would sample the baseline structure. The two beams can be distinguished using a variety of techniques, depending on the structure, the application scenario, etc. Several candidate techniques include FM or AM modulation spectroscopy (a carrier is used as a reference, and a sideband probes the resonance feature), dual-frequency absorption or phase measurements (e.g., using a frequency comb generator), temporal-domain techniques (such as frequency shift keying), etc.

In terms of the overall system configuration, the sensor can either have on-board sources, modulators and detectors or, it can be totally passive. The latter case may be desirable in that the cost of the sensor element would be drastically reduced, its power requirements essentially zero, and its weight significantly less than the active device. The passive device is, for example, remotely probed with a dual-beam scheme, and then discarded. In a battlefield scenario, this low-cost device can first be flown over a region to be probed for toxins using a μ-UAV, and then flown over another region where it can be probed (assuming that the desorption time constant is much longer than the in-flight transit time). The active device is more costly, but can have on-board processing and wireless networking capabilities, depending on the application scenario.

In order to detect a variety of substances with the same detector, a panelized approach can be used, as shown in FIG. 5(*a*). Each square 9(*a*)–9(*p*) represents an array of microcavities 2 having a different resonant frequency. The aggregate surface covers the entire spectrum of interest, whether the waves are visible, infrared, or teraherz area of the spectrum.

For a given region, the applied electric field of the probe beam 4 is only enhanced at the resonance frequency of that region; therefore, when the surface comes in contact with a substance having absorption lines which fall within the spectrum of the overall surface, only certain sections of the surface would register a positive result. When a compound 3 is encountered having a particular absorption spectrum, it will be detected in those regions where the resonance of the microcavities falls on one of the absorption peaks of the compound being detected, as shown by crosses in areas 9(*d*), 9(*i*), and 9(*n*).

A positive reading for a particular chemical or species requires a positive signal from certain sections of the detector. Only those sections for which the resonance frequency coincides with an absorption line of the substance would indicate a positive result, as shown on FIG. 5(*b*). From an example demonstrated on FIG. 5(*b*) one can see that only compounds 3 accumulated in the 9(*d*), 9(*i*) and 9(*n*) gave resonance peaks; therefore agents to be detected are only present in those three regions and nowhere else.

The identity of the compound 3 is determined by which regions detect the compound. Logic circuits embedded in the detector determine which species or chemical has been detected.

By combining the surface 1 having microcavities 2 with a broadband source 10 and a scanning detector 11, as shown in FIG. 6, the signal from each section of the surface 1 is measured. The panelized detecting surface 1 is amenable to monolithic fabrication in a compact package. The test surface 1 is illuminated, and the absorption of the various regions is monitored using the techniques described above and shown on FIGS. 5(*a*) and 5(*b*).

3. The Preferred Embodiments of the Sensor

A preferred embodiment of several such sensors, basic structure and principles of which are described above, is as follows.

To detect agents that absorb at optical frequencies, microcavities preferably comprise glass or polymer microspheres. These microspheres are formed in mono-disperse form, in which the spheres are all nearly the same size. The methods of fabrication of mono-disperse glass or polymer microspheres are known to those skilled in the art. If polymer microspheres are used, the preferred polymer is polystyrene. The state-selective material serves as an adhesive holding the microspheres in place on the surface of the substrate. Microspheres comprise just one type of optical resonant microcavities. It should be understood that any array of optical microcavities 2 can be used.

The size of the microcavities 2 is determined by the diameter of microspheres and is dictated by the wavelength of the absorption band of the agent to be detected 3. The range of diameters for such microspheres is preferably between about 10 micrometers and about 500 micrometers, depending on the material and wavelength of choice.

The microcavities 2 are designed so that they have a resonance at the same wavelength. A preferable geometry would be a cavity 2 in which the effective optical diameter is about one-half of wavelength, and the optical field forms a low-order mode within the microsphere. Alternatively, a cavity 2 is used in which the effective circumference is an integer multiple of half wavelengths, and the optical field forms a kind of whispering-gallery mode within the microsphere.

The microcavities 2 are preferably arranged on a planar optical waveguide 12, as shown on FIG. 7, in which one end 13 of the waveguide serves as the input for the light source 14, and the other end 15 serves as the output for the detector 16. This embodiment is shown on FIG. 7. The microcavities 2 in the form of microspheres 2(*a*) are coated with a material 5 that attracts the agent to be detected 3, and the detection is performed using a probe beam 4 as described earlier.

When the agent to be detected 3 comes in contact with the attracting agent 5, it is adsorbed on the surface of the microsphere 2(*a*). A wide variety of attracting agents can be used. An example of an attracting agent would be the same antibody for a particular antigen which may be produced naturally in the human body or produced synthetically. The glass substrate itself attracts many biological compounds, but is not selective. For selectivity, antibodies are preferably used.

These attracting agents are preferably applied by dissolving them at small concentration in the liquid containing the microspheres. Then, when the microspheres are applied to the substrate, they will already be coated with the attracting agent.

The optical field passing through the waveguide 12 excites each of the microspheres 2(*a*) through evanescent coupling, which in turn samples the agent 3 on the surface through evanescent coupling. The light signal traveling through the optical waveguide 12 is coupled into the microspheres 2(*a*) through evanescent fields 17.

The presence of the agent 3 is then registered as absorption of the optical signal. Since FIG. 7 shows many microspheres 2(*a*) in series, absorption in any single microsphere affects the overall signal level. This provides greater signal enhancement for a small concentration of the agent to be detected 3. For this reason, if a two-dimensional array of microspheres 2(*a*) is used, it is desirable to give the array a large aspect ratio, with the greatest possible number of microspheres 2(*a*) in series, while maintaining the necessary area. The number of microspheres 2(*a*) used is only limited by the size of detector that is desired, and can be as high as thousands or even millions of microspheres 2(a), depending on the detection area required.

Figure 8:
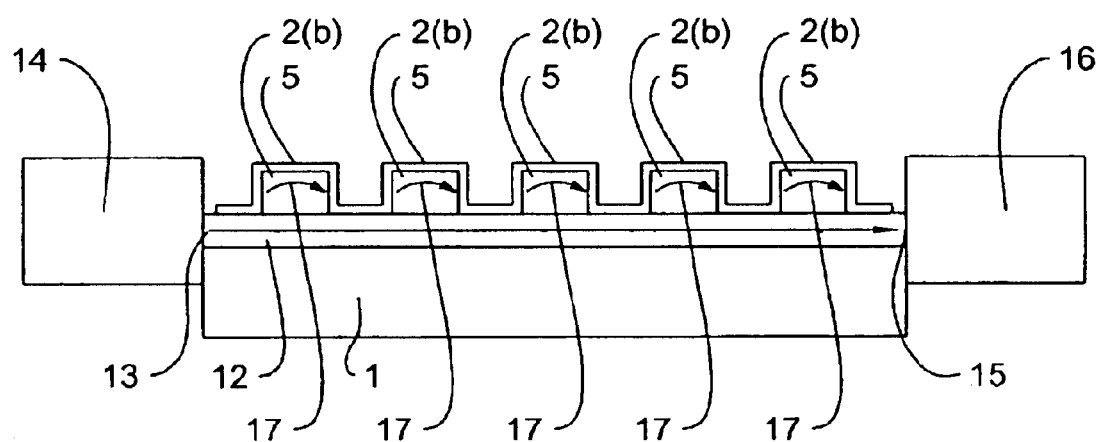
FIG. 8 is a schematic diagram showing an embodiment of the sensor, with microcavities etched into a dielectric material placed above a planar optical waveguide.

In another embodiment, shown on FIG. 8, which is also a preferred embodiment due to its low cost and ease of fabrication, the microcavities 2 comprise etched dielectric resonators 2(b), which are formed using standard photolithography or electron beam lithography techniques. These conventional photolithographic fabrication methods, such as, for instance, optical, electron beam, plasma etch, can be used to construct these devices. These methods are known to those skilled in the art.

The microcavities 2(b) so formed have an effective optical length of about one-half wavelength. This technique allows easier fabrication of uniform arrays with fewer defects. It also facilitates the forming of a tapered array (e.g., step-tapered array), as described earlier, to probe multiple frequencies. The microcavities 2(b) are arranged in a tapered linear array disposed on a substrate in which the resonance frequency of the cells varies across the array. The preferred materials for the substrate comprise glass and quartz. Light of each frequency is injected into a planar optical waveguide 12 waveguide at the correct point to couple into the column of microcavities 2(b) that resonate at that particular frequency.

Another method for exciting the tapered array of microcavities is to inject broadband light into the entire array, and then filter out the desired wavelength by placing a tapered filter before the detector. Only light that was at the resonant frequency of a given microcavity would couple into that microcavity 2 through evanescent fields 17. As before, the microcavities 2(b) are to be coated with a material 5 that attracts the agent to be detected 3. The preferred attracting material 5 is, as before, an antibody to the desired antigen to be detected.

Figure 9:
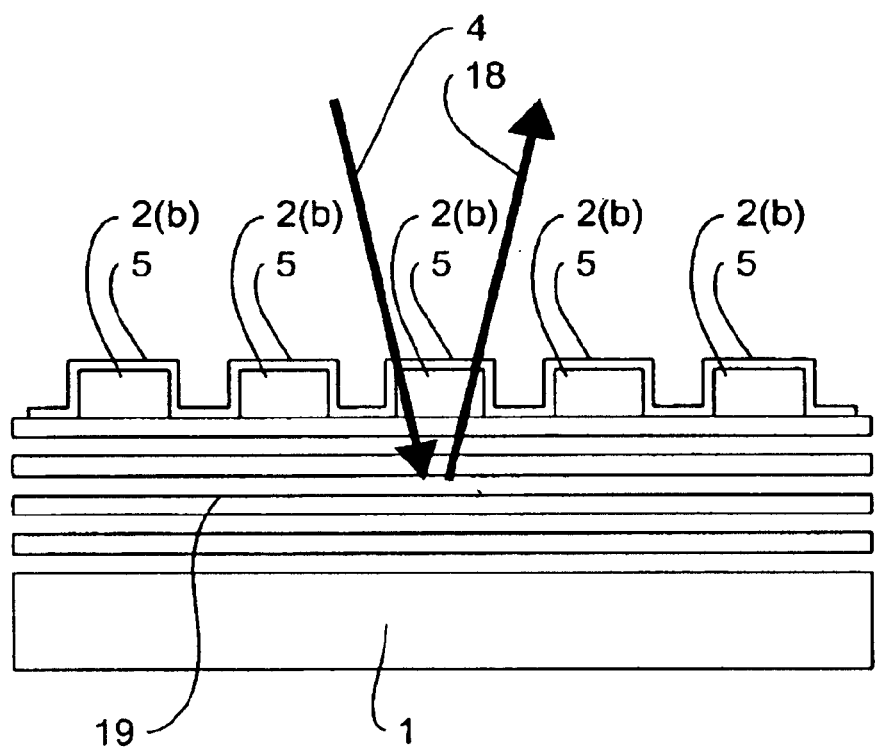
FIG. 9 is a schematic diagram showing a reflective version of the etched microcavity array.

Yet another possible geometry is an optical microcavity 2 which God is etched into a dielectric substrate 1 containing a dielectric mirror 18, as shown on FIG. 9.

The sensor of this embodiment operates in a reflection mode, with both the light source and detector being aimed at the array of microcavities 2(b), and the signal comprises the reflection from the microcavities. The probe beam 4 is directed at the array of microcavities 2(b), and the reflection is showed as the reflected 18. The microcavities 2(b) have an effective optical thickness equal to one-half wavelength.

The dielectric mirror 19 could be produced by chemical vapor deposition of alternating layers of two different dielectric materials. The chemical vapor deposition methodology is known to those skilled in the art. The preferred dielectric materials comprise glass, oxides of various metals, such as, for instance, titanium dioxide, and ceramic materials having alternate high and low dielectric constant. Semiconductor materials can also be used.

Each layer of the dielectric material has an effective thickness of one-quarter optical wavelength. The microcavities 2(b) are fabricated by etching trenches into a top layer of the dielectric material that is one-half wavelength thick.

Alternatively, the top layer of the dielectric material could be left un-etched to serve as one large cavity; however, in this alternative case, such large cavity would have less surface area than many small microcavities 2(b), which could decrease the sensitivity of the sensor. Either case could also have a taper introduced in the deposition process (not shown on FIG. 9), which would allow different regions of the microcavity 2(b) to resonate at different frequencies, for the detection of multiple resonances in the agent to be detected.

Superlattice structures, similar to those show on FIG. 2, can be used, in which case molecular beam epitaxial (MBE) or metal-oxide chemical vapor deposition (MO-CVD) techniques are preferably used to fabricate this class of device. The MBE and MO-CVD deposition methods are known to those skilled in the art.

Again, the microcavities 2(b) are coated with an attracting material 5 that attracts the agent to be detected 3 to the microcavities. As before, the antibodies are preferable attracting agents 5.

A variety of sensor configurations can be employed in the reflection-mode version of the sensor, discussed above and shown on FIG. 9., according to which the sensor is probed by a transceiver (i.e., the probe beam 4 and detection apparatus, not shown on FIG. 9, are co-located).

As an example, the structure can be configured as a retro-reflector corner-cube array or a "cat's eye" array. In the case of the "cat's eye" array, for example, a lenslet array focuses the radiation onto the surface of the microcavity array (located at the focal plane of the lenslet array). The probe beam 4 (optical, microwave, etc.) will, upon reflection from the structure, be directed into the retro-direction from which the beam initially arrived to the sensor. The "cat's eye" array is well known to those skilled in the art. A corner-cube array having a reflector positioned as a corner of a cube does the same thing as the "cat's eye" array.

This embodiment, having the "cat's eye" array, therefore automatically compensates for beam wander and device alignment, and assures that the return beam(s) from the sensor arrive back to the location of the initial source. The elements of the system are chosen to match the spectral region of operation. As an example, in the case of an optical system, a conventional lenslet array or dielectric coated mirror structure can be employed as the retro-reflector device.

Figure 10:
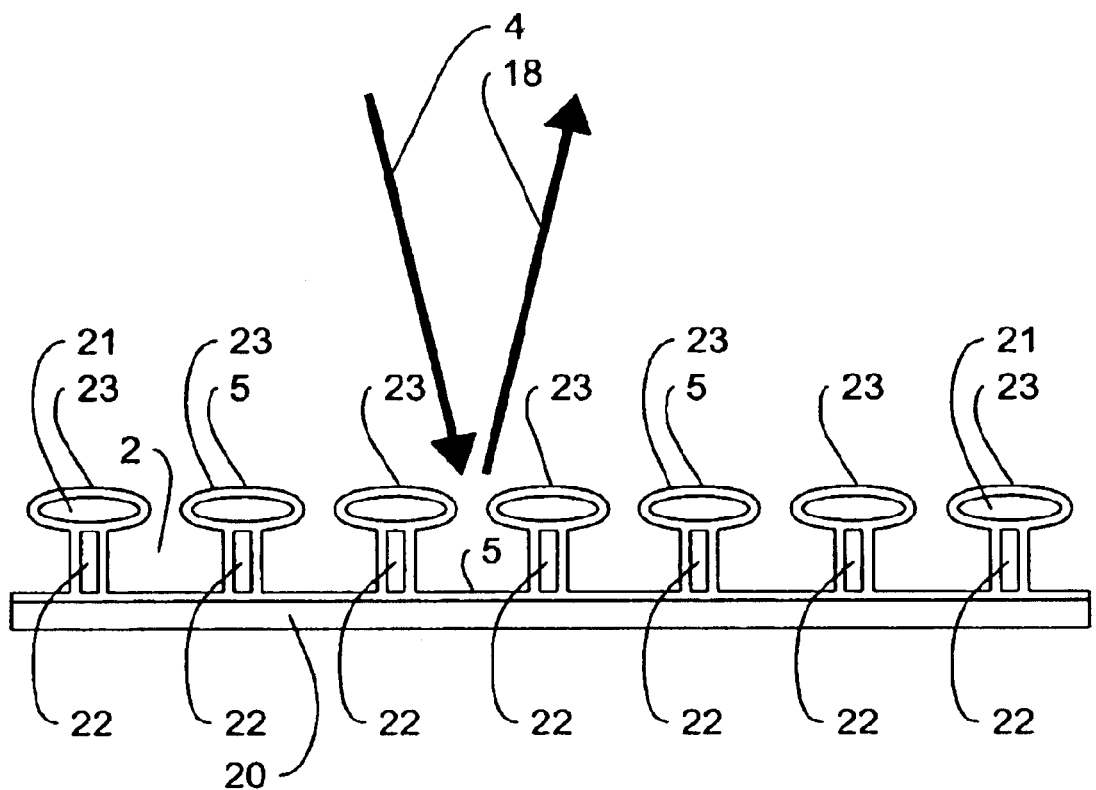
FIG. 10 is a schematic diagram showing a microwave version of the microresonators constructed out of a metal.

If the measurement is to be performed at microwave frequencies, then the structure can be made out of a metal, since metals have acceptably low loss at microwave frequencies. In this case, the structure comprises a high-impedance surface 20, having microcavities 2, as shown on FIG. 10. This is a metal surface 20 covered with a lattice of small resonators 21, each being much less than a wavelength in size. Conventional PC board fabrication techniques, known to those skilled in the art, can be used owing to the scale size of the features.

The resonators are formed by a combination of an effective capacitor and inductor, and the resonance frequency is given by the inverse square root of the product of the effective capacitance and inductance. The capacitance is determined by the distance between neighboring metal protrusions and the inductance is determined by their height.

Due to the presence of the resonance condition, the electric field of an incoming wave coming with the probe beam 4, is greatly enhanced in the region defined by the capacitors. It is enhanced by a factor equal to the Q of the structure, which is roughly equal to 377 divided by the square root of the ratio of the effective inductance over the effective capacitance. If the agent to be detected 3 falls within the capacitive region, and the resonance frequency of the microcavities 2 is near an absorption band of the agent to be detected 3, then the electromagnetic loss of the microcavities will be greatly enhanced. A material 5 that attracts the agent to be detected 3 may be placed within the capacitive region of the microcavities 2 to further enhance the loss by attracting more of the agent to be detected 3 into the capacitive region, that is, the region between the "mushroom" shapes.

The microwave version of the sensor may be constructed using one of several methods, depending on the frequency of operation. The structure preferably contains vertical metal posts 22, which support horizontal metal plates 23. The structure is preferably designed according to the following criteria.

The resonance frequency is $\omega=(LC)^{-1}$, where L is the inductance, and C is the capacitance.

$$L=\mu t;\ C=[\alpha \epsilon_{eff}/2\pi]\cdot \mathrm{Cos}\ h^{-1}(a/g),$$

wherein $\mu$ is the magnetic permeability of the material filling the interior of the structure, t is the thickness of the structure, a is the width of each metal plate, g is the gap between the plates, and $\epsilon_{eff}$ is the effective dielectric constant within the capacitive region.

The surface 20 is constructed using standard photolithography techniques on a sacrificial dielectric substrate. These photolithography techniques are known to those skilled in the art. Holes are etched or drilled through the substrate, and metal is plated through the holes and up onto the top surface. The top layer of metal is then patterned and etched to form the upper plates. The sacrificial dielectric layer is then dissolved to leave the exposed metal structure, which is coated with an attracting material 5.

In each of the above embodiments, the attracting material 5 to be used depends on the agent to be detected. If the agent is a biological species or a spore, then the attracting material is preferably an antibody to that species or spore.

As described above, these attracting agents include, but are not limited to, antibodies. The creation of materials that attract specific biological or chemical agents and enzymes is known to those skilled in the art of immunology or biology.

This invention is not limited to a specific agent or material, but is assumed to include any such agent to be detected 3, biological or otherwise, and a material for attracting it. Furthermore, the absorption of electromagnetic energy in the structures described above can occur either through the agent to be detected 3, or through the chemical combination of the attracting material 5 and the agent 3 when they come in contact.

Having described the invention in connection with several embodiments thereof, modification will now suggest itself to those skilled in the art. As such, the invention is not to be limited to the described embodiments except as required by the appended claims.

We claim:

1. A sensor for detecting chemical and/or biological compounds, said sensor comprising:
   (a) a first element comprising a plurality of microcavities disposed on a substrate; and
   (b) a second element comprising a source of electromagnetic radiation and a detector of electromagnetic radiation,
   wherein said chemical and/or biological compounds are adsorbed or/and absorbed by said microcavities causing a change of electromagnetic field of said microcavities, said change being detected by said second element.

2. The sensor of claim 1, wherein said second element directs a probe beam emanated from said source of electromagnetic radiation at said plurality of microcavities and said detector of electromagnetic radiation detects a reduction in electromagnetic energy carried by a beam reflected off and/or passed through said plurality of microcavities compared with electromagnetic energy carried by said probe beam.

3. The sensor of claim 1, wherein all said microcavities resonate at a same frequency.

4. The sensor of claim 1, wherein selective ones of said microcavities resonate at different frequencies.

5. The sensor of claim 1, wherein said source of electromagnetic radiation comprises lasers and ultraviolet spectral regions, and optical light sources.

6. The sensor of claim 1, wherein said detector comprises photodetectors, said photodetectors operating at a range of frequencies comprising microwave, teraherz, infrared, visible light and ultra-violet ranges of frequencies.

7. The sensor of claim 1, wherein a Q of said microcavities is within a range between about a few thousand to more than about ten million.

8. The sensor of claim 1, wherein said plurality of microcavities is arranged in patterns, said patterns comprising a tri-dimensional lattice, a two-dimensional array and a super-lattice structure.

9. The sensor of claim 1, wherein said microcavities are furthercoated with a state-selective material attracting said chemical and/or biological compounds.

10. The sensor of claim 1, wherein said second element comprises a retro-reflector corner-cube array and a "cat's eye" array.

11. The sensor of claim 3, wherein said microcavities comprise microspheres.

12. The sensor of claim 3, wherein said microcavities have an effective optical diameter of about 50% of a wavelength at which said microcavities resonate.

13. The sensor of claim 4, wherein said microcavities comprise etched dielectric resonators.

14. The sensor of claim 4, wherein said microcavities have an effective optical diameter of about 50% of a wavelength at which said microcavities resonate.

15. The sensor of claim 4, wherein said substrate comprises a dielectric substrate, said dielectric substrate having a top layer and an underlying layer and further comprising a dielectric mirror, said plurality of microcavities being etched into said top layer of said dielectric substrate.

16. The sensor of claim 5, wherein said lasers further comprise lasers operating in visible, infrared, or ultraviolet spectral regions.

17. The sensor of claim 5, wherein said optical light sources further comprise light emitting diodes, incandescent, fluorescent, and phosphorescent sources.

18. The sensor of claim 6, wherein said photodetectors further comprise photodiodes.

19. The sensor of claim 6, wherein a measurement is performed at said microwave range of frequencies, and wherein said sensor comprises:
   (a) said substrate fabricated of a material, said material comprising metals;
   (b) vertical metal posts;
   (c) horizontal metal plates supported by said vertical metal posts; and
   (d) a lattice of resonators disposed upon said substrate.

20. The sensor of claim 11, wherein said microcavities have an effective optical diameter of about 50% of a wavelength at which said microcavities resonate.

21. The sensor of claim 11, wherein said plurality of microspheres is arranged on a planar optical waveguide.

22. The sensor of claim 11, wherein said chemical and/or biological compounds absorb electromagnetic energy at optical frequencies and wherein said microspheres are manufactured of a material comprising glass or polymers.

23. The sensor of claim 11, wherein said electromagnetic field of said microspheres forms a whispering-gallery mode and said microspheres have an effective circumference which is an integer multiple of half wavelength at which said microspheres resonate.

24. The sensor of claim 13, wherein said etched dielectric resonators are arranged in a tapered linear array.

25. The sensor of claim 15, wherein said dielectric substrate has a thickness equal to about 50% of a wavelength at which said microcavities resonate.

26. The sensor of claim 15, wherein said microcavities comprise said top layer of said dielectric substrate, said top layer remaining un-etched.

27. The sensor of claim 19, wherein said resonator comprises a capacitor and an inductor.

28. The sensor of claim 22, wherein said microspheres are fabricated in a mono-disperse form.

29. The sensor of claim 28, wherein said microspheres have a diameter within a range of between about 10 micrometers and about 500 micrometers.

30. A method for detecting chemical and/or biological compounds, said method comprising steps of:
   (a) providing a substrate with a plurality of microcavities disposed thereupon;
   (b) providing a probing device comprising a source of electromagnetic radiation and a detector of electromagnetic radiation;
   (c) directing said chemical and/or biological compounds at said microcavities;
   (d) adsorbing or/and absorbing said chemical and/or biological compounds by said microcavities causing a change of electromagnetic field of said microcavities; and
   (e) detecting said change of electromagnetic field by said probing device.

31. The method of claim 30, wherein said step of said detecting of said change by said probing device comprises further steps of:
   (a) directing a probe beam emanated from said source of electromagnetic radiation at said plurality of microcavities; and
   (b) using said detector of electromagnetic radiation, detecting a reduction in electromagnetic energy carried by a beam reflected off and/or passed through said plurality of microcavities compared with electromagnetic energy carried by said probe beam.

32. The method of claim 30, wherein in said step of providing said substrate with said plurality of microcavities, all said microcavities resonate at a same frequency.

33. The method of claim 30, wherein in said step of providing said substrate with said plurality of microcavities, selected ones of said microcavities resonate at different frequencies.

34. The method of claim 30, wherein in said step of providing said substrate with said plurality of microcavities, a Q of said microcavities is within a range between about a few thousand to more than about ten million.

35. The method of claim 30, wherein in said step of providing said substrate with said plurality of microcavities, said plurality of microcavities is arranged in patterns comprising a tri-dimensional lattice, a two-dimensional array and a super-lattice structure.

36. The method of claim 30, wherein said in said step of providing said substrate with said plurality of microcavities, said microcavities are further coated with a state-selective material attracting selected ones of said chemical and/or biological compounds.

37. The method of claim 30, wherein in said step of providing said probing device, said source of electromagnetic radiation comprises lasers and optical light sources.

38. The method of claim 30, wherein in said step of providing said probing device, said detector comprises photodetectors, said photodetectors operating at a range of frequencies comprising microwave and teraherz ranges of frequencies.

39. The method of claim 30, wherein said step of directing said chemical and/or biological compounds at said microcavities is accomplished by using one or more methods comprising:
   (a) pumping air suspected of containing said chemical and/or biological compounds over said microcavities;
   (b) pumping a liquid suspected of containing said chemical and/or biological compounds over said microcavities; and
   (c) rapid aeration of said liquid suspected of containing said chemical and/or biological compounds.

40. The method of claim 32, wherein in said step of providing said substrate with said plurality of microcavities, said microcavities comprise microspheres.

41. The method of claim 32, wherein in said step of providing said substrate with said plurality of microcavities, said microcavities have an effective optical diameter of about 50% of a wavelength at which said microcavities resonate.

42. The method of claim 33, wherein in said step of providing said substrate with said plurality of microcavities, said microcavities comprise etched dielectric resonators.

43. The method of claim 33, wherein in said step of providing said substrate with said plurality of microcavities, said microcavities have an effective optical diameter of about 50% of a wavelength at which said microcavities resonate.

44. The method of claim 33, wherein in said step of providing said substrate with said plurality of microcavities, said substrate comprises a dielectric substrate, said dielectric substrate having a top layer and an underlying layer and further comprising a dielectric mirror, said plurality of microcavities being etched into said top layer of said dielectric substrate.

45. The method of claim 37, wherein in said step of providing said probing device, said lasers further comprise lasers operating in visible, infrared, or ultraviolet spectral regions.

46. The method of claim 37, wherein in said step of providing said probing device, said optical light sources further comprise light emitting diodes, incandescent, fluorescent, and phosphorescent sources.

47. The method of claim 38, wherein in said step of providing said probing device, said photodetectors further comprise photodiodes.

48. The method of claim 38, wherein in said step of providing said probing device and wherein a measurement is performed at said microwave range of frequencies, said sensor further comprises:
   (a) said substrate fabricated of a material, said material comprising metals;
   (b) vertical metal posts;
   (c) horizontal metal plates supported by said vertical metal posts; and
   (d) a lattice of resonators disposed upon said substrate.

49. The method of claim 39, wherein said pumping of air and/or of said liquid is achieved by using devices comprising conventional pumps and microelectromechanical devices.

50. The method of claim 40, wherein in said step of providing said substrate with said plurality of microcavities, said microcavities have an effective optical diameter of about 50% of a wavelength at which said microcavities resonate.

51. The method of claim 40, wherein in said step of providing said substrate with said plurality of microcavities, said plurality of microspheres is arranged on a planar optical waveguide.

52. The method of claim 40, wherein in said step of providing said substrate with said plurality of microcavities, said chemical and/or biological compounds absorb electromagnetic energy at optical frequencies and wherein said microspheres are manufactured of a material comprising glass or polymers.

53. The method of claim 40, wherein in said step of providing said substrate with said plurality of microcavities, said electromagnetic field of said microspheres forms a whispering-gallery mode and said microspheres have an effective circumference which circumference is an integer multiple of half wavelength at which said microspheres resonate.

54. The method of claim 42, wherein in said step of providing said substrate with said plurality of microcavities, said etched dielectric resonators are arranged in a tapered linear array.

55. The method of claim 44, wherein in said step of providing said substrate with said plurality of microcavities, said dielectric substrate has a thickness equal to about 50% of a wavelength at which said microcavities resonate.

56. The method of claim 44, wherein in said step of providing said substrate with said plurality of microcavities, said microcavities comprise said top layer of said dielectric substrate, said top layer remaining un-etched.

57. The method of claim 48, wherein in said step of providing said probing device, said resonator comprises a capacitor and an inductor.

58. The method of claim 52, wherein in said step of providing said substrate with said plurality of microcavities, said microspheres are fabricated in a mono-disperse form.

59. The method of claim 58, wherein in said step of providing said substrate with said plurality of microcavities, said microspheres have a diameter within a range of between about 10 micrometers and about 500 micrometers.

* * * * *